(12) United States Patent
Kohls et al.

(10) Patent No.: US 7,593,764 B2
(45) Date of Patent: Sep. 22, 2009

(54) SYSTEM AND METHOD OF SERIAL COMPARISON FOR DETECTION OF LONG QT SYNDROME (LQTS)

(75) Inventors: Mark Kohls, New Berlin, WI (US); Ian Rowlandson, Milwaukee, WI (US); Joel Xue, Germantown, WI (US)

(73) Assignee: General Electric Company, Schenectady, NY (US)

( * ) Notice: Subject to any disclaimer, the term of this patent is extended or adjusted under 35 U.S.C. 154(b) by 309 days.

(21) Appl. No.: 11/538,353

(22) Filed: Oct. 3, 2006

(65) Prior Publication Data

US 2008/0082016 A1 Apr. 3, 2008

(51) Int. Cl.
*A61B 5/0402* (2006.01)
(52) U.S. Cl. ...................... 600/509; 600/516
(58) Field of Classification Search ............... 600/509, 600/516
See application file for complete search history.

(56) References Cited

U.S. PATENT DOCUMENTS

| | | | |
|---|---|---|---|
| 2002/0029002 A1 | 3/2002 | Bardy | |
| 2002/0133495 A1* | 9/2002 | Rienhoff et al. | 707/100 |
| 2004/0086886 A1* | 5/2004 | Goldstein | 435/6 |
| 2005/0177049 A1* | 8/2005 | Hardahl et al. | 600/509 |
| 2005/0234352 A1 | 10/2005 | Bardy | |
| 2006/0079795 A1 | 4/2006 | Busche et al. | |
| 2006/0259992 A1* | 11/2006 | Koren et al. | 800/14 |

FOREIGN PATENT DOCUMENTS

| | | |
|---|---|---|
| EP | 1 110 503 A2 | 6/2001 |
| WO | 01/67950 A1 | 9/2001 |

OTHER PUBLICATIONS

Search Report dated Feb. 4, 2008.

\* cited by examiner

*Primary Examiner*—Scott M Getzow
(74) *Attorney, Agent, or Firm*—Andrus, Sceales, Starke & Sawall, LLP

(57) ABSTRACT

The present disclosure includes a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patients ECG to these databases will facilitate the detection of such occurrences as changes in QT interval from success of ECGs, changes in T-wave morphology, changes in U-wave morphology and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

17 Claims, 2 Drawing Sheets

SYSTEM AND METHOD OF SERIAL COMPARISON FOR DETECTION OF LONG QT SYNDROME (LQTS)

FIELD OF THE DISCLOSURE

The present disclosure relates to the field of diagnostic cardiology. More particularly, the present disclosure relates to the field of detecting long QT syndrome (LQTS).

BACKGROUND OF THE DISCLOSURE

New prescription drugs follow a rigorous process from compound discovery to final approval requiring many years and many millions of dollars in investment. During clinical trials, much ECG data is acquired from the patients involved in the trial. Typically, these ECGs are reviewed in a "blinded" fashion by the overreader. In other words, the person reading the ECG is completely obscured from the demographic information of the patient and may not have access to the patient's previous ECGs to prevent biasing during the overreading process. While this technique is useful to increase the accuracy of the process, from the patient's perspective it may cause the overreader or trial administrator to miss significant changes in the ECG.

Additionally, in normal hospital or clinical practices, ECGs are typically reviewed in reverse chronological order, in other words, from latest to earliest to look for changes in the ECG. This technique is typically used to look for serial changes common in myocardial infarction and ischemic heart disease. However, it is now understood that many drugs can cause acquired LQTS in patients over time, thus making it useful to have an automated method to detect acquired (drug-induced) LQTS.

Furthermore, congenital LQTS is well understood to be a cause of Sudden Cardiac Death. The prevalence of this condition in the population is typically estimated at 1 in 10,000 patients. However, recent studies have shown that the prevalence and types of mutations between ethnic groups varies and could be much greater than this ratio in some groups. Sudden Cardiac Death kills more than 1000 individuals each day in the U.S. It would be useful to have a system that could identify these patients before an arrhythmic episode.

SUMMARY OF THE DISCLOSURE

The present disclosure includes a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patients ECG to these databases will facilitate the detection of such occurrences as changes in QT interval from successive ECGs, changes in T-wave morphology, changes in U-wave morphology and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

One aspect of the present disclosure is a method of detecting a long QT syndrome in a patient, the method comprising acquiring a set of ECG data from the patient, comparing the set of ECG data to a set of ECG characteristic data stored in a plurality of databases, wherein the comparing step is configured to identify any characteristics in the set of ECG data that are emblematic of LQTS and adjusting an interpretation of the set of ECG data when a characteristic is found in the set of ECG data, such that the adjustment corresponds to the characteristic. The method further comprises making the interpretation prior to the adjusting step and sending the set of ECG data to a centralized storage system wherein the plurality of databases includes a previous ECG database, and wherein the comparing step includes identifying any significant change in a QT interval. The plurality of databases includes a known acquired LQTS characteristics database, wherein the comparing step includes identifying a significant characteristic in the set of ECG data with respect to a known acquired characteristic and identifying a significant characteristic in the set of EGC data with respect to a known genetic characteristic. The method further comprises updating the interpretation in the centralized storage system, adding the set of ECG data to any of the plurality of databases and outputting the interpretation to a user.

Another aspect of the present disclosure is a system for detecting a long QT syndrome in a patient, the system comprises an ECG acquisition system configured to collect a set of ECG data from the patient, a storage media for storing a computer application, a processor coupled to the ECG acquisition system and the storage media, and configured to execute the computer application, and further configured to receive the set of ECG data from the ECG acquisition system, wherein when the computer application is executed, the set of ECG data is compared to a set of ECG characteristic data in a plurality of databases, any characteristics in the set of ECG data that are emblematic of LQTS are identified, and an interpretation of the set of ECG data is adjusted when a characteristic is identified in the set of ECG data, such that the adjustment corresponds to the characteristic. The interpretation of the system is made prior to the adjusting step and farther comprises a centralized storage system wherein the set of ECG data is sent to the centralized storage system. The plurality of databases includes a previous ECG database, wherein when the computer application is executed, any significant change in a QT interval is identified. The plurality of databases includes a known acquired LQTS characteristics database, wherein when the computer application is executed, a significant characteristic in the set of ECG data with respect to a known acquired characteristic is identified and a known genetic characteristic is identified. The interpretation is updated in the centralized storage system and the set of ECG data is added to any of the plurality of databases. The system further comprises an output device configured for outputting the interpretation to a user.

DETAILED DESCRIPTION

Figure 1:
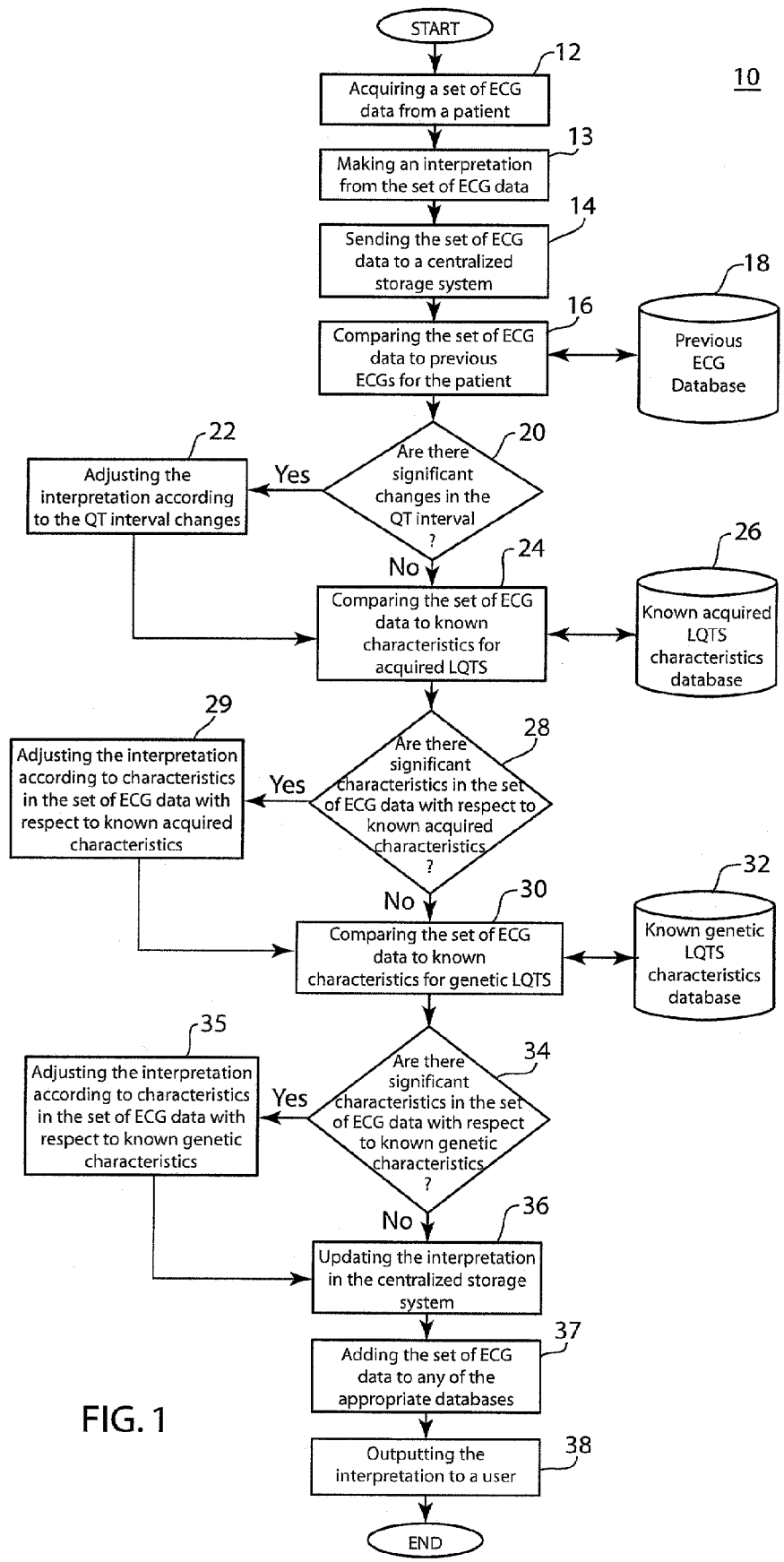
FIG. 1 illustrates a flow chart according to an embodiment of the present method.

The present disclosure includes a system and method configured to flag significant changes in the duration of a QT interval and T wave morphology of a patient, and furthermore the shape of the QRS-complex and detect the presence or absence of U-waves. The system and method is further configured to report any detected information by adjusting an interpretation of the patient's ECG. The system and method is preferably embodied in a computer software application and can accurately detect and report changes in the patient's QT interval and T wave morphology over time from successing resting ECGs. The system and method of the present disclosure will include a number of databases configured to store previous ECGs of the patient, known acquired LQTS characteristics, and known genetic LQTS characteristics. These databases will include gender specific duration and morphology characteristics as it is well-known that, in general, women have longer QT intervals, as well as ethnicity specific characteristics as changes in duration and morphology have been shown to variant frequency and type based on genetics and ancestry. The databases will also include drug information and those drugs defined effects on QT duration, the likelihood of producing torsades, and other ECG effects, for example, significant Ikr reduction can be linked to T wave flat, reduced curvature in the front portion of T wave, and T wave norches; and significant reduction of Iks can be linked to symmetrical T wave, early onset of T wave. Those morphology features can be used as an additional information to QT interval prolongation when we detect abnormal drug induced repolarization changes. Such characteristics will be stored in the known acquired LQTS database and the system and method is configured to pattern match against such drug characteristics and look for specific changes associated with those drugs.

As stated previously, the system and method may accurately detect or import changes in QRS morphology, U-wave morphology, as well as match against electrocardiograph characteristics of known genetic variations in LQTS.

It is also important to note that the system and method is configured to be integrated into existing ECG management systems currently installed in hospitals and clinics, and furthermore integrated into an ECG that is capable of storing multiple ECGs for a single patient. Preferably, the MUSE system, which is an ECG management system produced by GE Healthcare, is a system for which the present system and method is configured to be integrated into.

The system and method of the present disclosure also adjust an original interpretation of the patient's ECG data with the findings of the database analysis. The interpretation will not only be adjusted in order to make it more accurate, but the patient's ECG data will also be added back into the databases as appropriate. In other words, the patient's ECG data will be labeled and inserted into the patient's previous ECG database, and appropriately placed in the known acquired LQTS characteristics database and the known genetic LQTS characteristics database. Furthermore, the system and method is capable of flagging outliers for further review by a study director. System and method is configured to locate ECG tracing where the computer detected a different serial, evolving pattern than the overreader. Once these outliers are located, a tool determines and assists the study director in establishing consistency in the reading of the ECGs. In other words, the consistency in overreading of specific ECG patterns in a study population is examined, and this tool detects the consistency of reading the same T-wave pattern if it is maintained for a specific patient. Lastly, the tool helps the study supervisor determine if particular tracings had been properly assessed.

Referring now to FIG. 1, an embodiment of the detection method 10 is depicted. In step 12, a set of ECG data is acquired from a patient. The acquiring of such ECG data is effectuated by any known method or system known in the art, and is preferably facilitated when the patient is in a resting state. In step 13, an initial interpretation is made by an overreader of the set of ECG data. In this step, the interpretation is an initial evaluation of how the patient's heart is functioning by making the reading of the ECG that would normally occur by an overreader. In step 14, the set of ECG data is sent to a centralized storage system, wherein the centralized storage system is one known in the art and can include centralized storage systems that are part of existing hospital ECG management systems.

In step 16, the set of ECG data is compared to previous ECGs for that patient. The set of ECG data is compared to previous ECGs and the previous ECG database 18. If in step 20, if it is found that there are significant changes in the QT interval from the comparing step 16 to the previous ECG database 18, then in step 22 the interpretation is adjusted according to the QT interval changes. If there are no significant changes in the QT interval in step 20, then the detection method 10 moves onto step 24. Likewise, after the adjusting step 22, the method moves to step 24. In step 24, the set of ECG data is compared to known characteristics for acquired LQTS that are contained in the known acquired LQTS characteristics database 26. As discussed above, this known acquired LQTS characteristics database 26 can include characteristic ECGs from patients that were taking specific drugs, and can be further coupled to a complete drug database to accurately identify those drugs for the user. In step 28, if there are significant characteristics in the set of ECG data with respect to known acquired characteristics, then the interpretation is once again adjusted according to the characteristics in the set of ECG data with respect to the know acquired characteristics in step 29. After this adjustment, the method continues on to step 30. If in step 28, there are no significant characteristics in the set of ECG data with respect to known acquired characteristics, then the method continues onto step 30 as well. In step 30, the set of ECG data is compared to known characteristics for genetic LQTS, with a known genetic LQTS characteristics database 32. As discussed above, this known genetic LQTS characteristic database includes characteristic ECG patterns according to such things as gender, ethnicity, and ancestry, among others. In step 34, if there are significant characteristics in the set of ECG data with respect to known genetic characteristics, then the interpretation is once again adjusted in step 35 according to characteristics in the set of ECG data with respect to known genetic characteristics, and the method 10 moves on to step 36. If there are no significant characteristics in the set of ECG data with respect to known genetic characteristics, then the method can likewise move onto step 36.

In step 36, the interpretation is updated in the centralized storage system to reflect any adjustments made in steps 35, 29, or 22. In step 37, the set of ECG data is added to any of the appropriate databases 32, 26, 18. Finally, in step 38, the interpretation is outputted to a user such as a physician or other hospital personnel, and may be outputted by displaying the interpretation on a video screen or printed as a report or as part of the ECG graphical printout, or in any other way known to one skilled in the art. It should be noted that an embodiment of this method may operate without some of the steps described above. For example, the initial interpretation made in step 13 may be omitted, and the method 10 may create an interpretation from any adjustments made in steps 22, 29 or 35. Furthermore, the set of ECG data may be sent and stored in something other than a centralized storage system in step 14. The detection method 10 may also be modified to include additional, or to omit any of the databases 18, 26, 32 according to the needs of the user. As in step 14, the final updating of the interpretation in step 36 also does not need to be done in the central storage system, and may be effectuated in another area of an ECG management system. Lastly, it is contemplated that the user of the system and method of the present disclosure may select that the set of ECG data not be added to any of the appropriate databases after an interpretation is updated in step 37.

Figure 2:
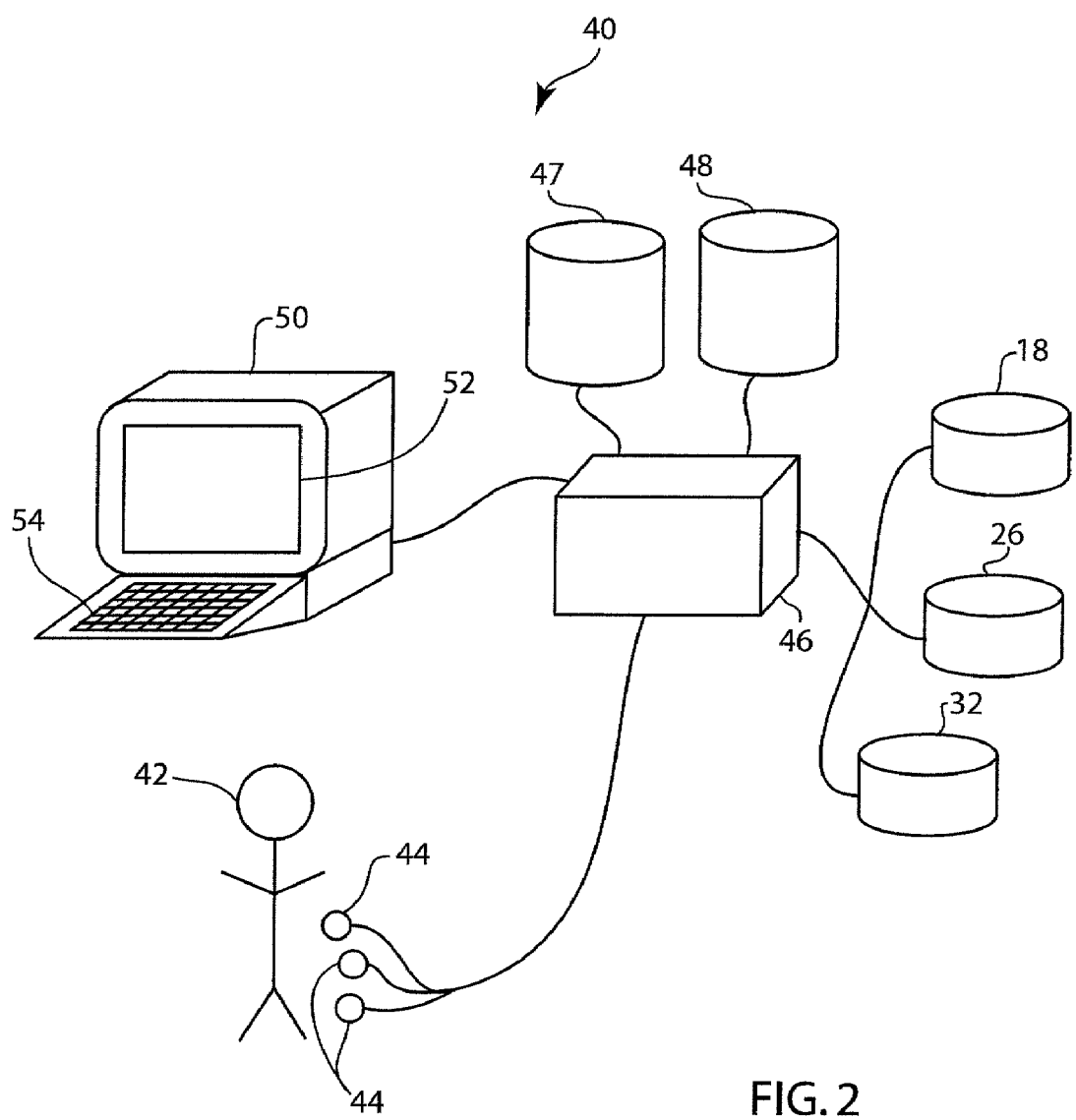
FIG. 2 illustrates a block diagram according to an embodiment of the present system.

FIG. 2 depicts a block diagram of an embodiment of the detection system 40. Here, an ECG acquisition system 44 known in the art, is attached to a patient 42 and a set of ECG data is acquired from the patient 42. A computer software application is stored in a storage media 47, and executed on a processor 46. When executed, the computer software application effectuates the method as described above. It has been contemplated that the detection system 40 as depicted and described may include or be implemented with an existing hospital ECG management system, or may even stand alone. Referring back to FIG. 2, the acquired ECG data from the patient 42 is stored in the central storage system 48, and the processor 46, executing the computer software application, proceeds to compare the acquired ECG data in the centralized storage system to the previous ECG data in the previous ECG database 18, the known acquired LQTS characteristics in the known acquired LQTS characteristics database 26, and the known genetic LQTS characteristics in the known genetic LQTS characteristics database 32. It should be noted that prior to making these comparisons, the computer software application may make an initial interpretation from the set of ECG data. As described above, these databases are utilized to see whether there are significant changes in the QT interval, significant characteristics in the set ECG data with respect to known acquired characteristics, or to determine whether there are significant characteristics in the set of ECG data with respect to known genetic characteristics. If any changes or significant characteristics appear in the ECG data, then the computer application executing the method will adjust the interpretation in the centralized storage system 48.

The detection system 40 also includes a user interface device 50, having a graphical user interface (GUI) 52 and an input device 54. This user interface device 50 may also include a printer (not shown) or other output device for outputting the interpretation to a physician or other system user. The input 54 and GUI 52 allow a user to view the interpretation and other ECG results on the screen of a user interface device 50 such as a terminal (as shown), or alternative user interface devices 50 such as PDAs, medical monitors, or any other known user interface devices 50 in the art. Still referring to FIG. 2, the detection system 40, executing the computer software application, is configured to add the set of ECG data to any of the appropriate databases, 18, 26, 32 as may be selected by a user. The connection between detection system and centralized database server can be wired or wireless. The communication is bidirectional between the detection system and the database system. The serial comparison and interpretation is performed in the database system and the results can be sent back to the detection system if required. All those processes are transparent from the user as if all processing are happened in the same system and the same location.

The system and method as described has significant advantages over the prior art. The system and method enables the detection of congenital LQTS, possibly including matching to known genetic markers. The system and method also enables the detection of acquired "drug-induced" LQTS in patients and clinical trials or normal clinical practice, the accurate use of drug information and analyzing ECGs. Finally, the system and method enables mining of data for adverse event tracking when individual aggregated into a database.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of detecting a long QT syndrome in a patient, the method comprising:

acquiring a set of ECG data from the patient;

comparing the set of ECG data to a set of ECG characteristic data stored in a plurality of databases, wherein the comparing step is configured to identify any characteristics in the set of ECG data in any of the plurality of databases that are emblematic of LQTS, and further wherein the plurality of databases includes a previous ECG database, wherein the previous ECG databases includes a set of previous ECG data of the patient, and further wherein the comparing step includes identifying any significant change in a QT interval; and adjusting an interpretation of the set of ECG data after comparing the ECG data to any of the plurality of databases when a characteristic is found in the set of ECG data in any of the plurality of databases, such that the adjustment corresponds to the characteristic.

2. The method according to claim 1, further comprising making the interpretation prior to the adjusting step.

3. The method according to claim 1, further comprising sending the set of ECG data to a centralized storage system.

4. The method according to claim 1, wherein the plurality of databases includes a known acquired LQTS characteristics database, wherein the comparing step includes identifying a significant characteristic in the set of ECG data with respect to a known acquired characteristic.

5. The method according to claim 1, wherein the plurality of databases includes a known genetic LQTS characteristics database, wherein the comparing step includes identifying a significant characteristic in the set of EGC data with respect to a known genetic characteristic.

6. The method according to claim 1, further comprising updating the interpretation in the centralized storage system.

7. The method according to claim 1, further comprising adding the set of ECG data to any of the plurality of databases.

8. The method according to claim 1, further comprising outputting the interpretation to a user.

9. A system for detecting a long QT syndrome in a patient, the system comprising:

an ECG acquisition system configured to collect a set of ECG data from the patient;

a storage media for storing a computer application;

a processor coupled to the ECG acquisition system and the storage media, and configured to execute the computer application, and further configured to receive the set of ECG data from the ECG acquisition system, wherein when the computer application is executed, the set of ECG data is compared to a set of ECG characteristic data in each of a plurality of databases, and when any characteristics in the set of ECG data that are emblematic of LQTS, an interpretation of the set of ECG data is adjusted, such that the adjustment corresponds to the characteristic, further wherein the adjustment is made after the set of ECG data is compared to each one of the plurality of databases, and further wherein the plurality of databases includes a previous ECG database, wherein the previous ECG databases includes a set of previous ECG data of the patient, and further wherein when the computer application is executed, any significant change in a QT interval is identified.

10. The system according to claim 9, wherein the interpretation is made prior to the adjusting step.

11. The system according to claim 9, further comprising a centralized storage system wherein the set of ECG data is sent to the centralized storage system.

12. The system according to claim 9, wherein the plurality of databases includes a known acquired LQTS characteristics database, wherein when the computer application is executed, a significant characteristic in the set of ECG data with respect to a known acquired characteristic is identified.

13. The system according to claim 9, wherein the plurality of databases includes a known genetic LQTS characteristics database, wherein when the computer application is executed, a significant characteristic in the set of EGC data with respect to a known genetic characteristic is identified.

14. The system according to claim 9, wherein the interpretation is updated in the centralized storage system.

15. The system according to claim 9, wherein the set of ECG data is added to any of the plurality of databases.

16. The system according to claim 9, further comprising an output device configured for outputting the interpretation to a user.

17. A method of detecting a long QT syndrome in a patient, the method comprising:

acquiring a set of ECG data from the patient;

comparing the set of ECG data to a first set of ECG characteristic data stored in a previous ECG database, wherein the previous ECG databases includes a set of previous ECG data of the patient, and further wherein comparing the set of ECG data to the first set of ECG characteristic data identifies any significant change in a QT interval;

comparing the set of ECG data to a second set of ECG characteristic data stored in a known acquired LQTS characteristics database, wherein comparing the set of ECG data to the second set of ECG characteristics data identifies a significant characteristic in the set of ECG data with respect to a known acquired characteristic;

comparing the set of ECG data to a third set of ECG characteristic data stored in a known genetic LQTS characteristics database, wherein comparing the set of ECG data to the third set of ECG characteristic data identifies a significant characteristic in the set of ECG data with respect to a known genetic characteristic; and adjusting an interpretation of the set of ECG data when a characteristic is found in any of the sets of ECG data, such that the adjustment corresponds to the characteristic, and further wherein the adjustment is made after each comparison step.

\* \* \* \* \*